United States Patent
Contel et al.

(10) Patent No.: US 9,315,531 B2
(45) Date of Patent: Apr. 19, 2016

(54) TITANOCENE-GOLD DERIVATIVES COMPRISING THIOLATO LIGANDS

(71) Applicant: Research Foundation of the City University of New York, New York, NY (US)

(72) Inventors: Maria Contel, Brooklyn, NY (US); Jacob Fernandez-Gallardo, Brooklyn, NY (US); Benelita T. Elie, Brooklyn, NY (US); Joe W. Ramos, Honolulu, HI (US)

(73) Assignees: Research Foundation of the City University of New York, New York, NY (US); University of Hawaii, Honolulu, HI (US)

( * ) Notice: Subject to any disclaimer, the term of this patent is extended or adjusted under 35 U.S.C. 154(b) by 0 days.

(21) Appl. No.: 14/731,842

(22) Filed: Jun. 5, 2015

(65) Prior Publication Data
US 2015/0353591 A1   Dec. 10, 2015

Related U.S. Application Data

(60) Provisional application No. 62/008,272, filed on Jun. 5, 2014.

(51) Int. Cl.
C07F 17/02 (2006.01)
C07F 7/28 (2006.01)
C07F 9/50 (2006.01)

(52) U.S. Cl.
CPC . *C07F 17/02* (2013.01); *C07F 7/28* (2013.01); *C07F 9/50* (2013.01)

(58) Field of Classification Search
CPC ............... C07F 17/02; C07F 7/28; C07F 9/50
USPC ......................................................... 514/102
See application file for complete search history.

(56) References Cited

PUBLICATIONS

Fernandez-Gallardo et al.; Organometallic Titanocene-Gold Compounds as Potential Chemotherapeutics in Renal Cancer. Study of their Protein Kinase Inhibitory Properties; Organometallics; Oct. 30, 2014; pp. 6669-6681; US.

Gonzalez-Pantoja, Jose et al.; Titanocene-Phosphine Derivatives as Precursors to Cytotoxic Heterometallic TiAu2 and TiM (M = Pd, Pt) Compounds. Studies of Their Interactions with DNA; Inorganic Chemistry; Sep. 29, 2011; pp. 11099-11110; vol. 50; American Chemical Society; US.

Edwards, Dennis A et al.; Diphenylphosphinoacetate, nicotinate and thiophenoxyacetate as bridging ligands in heterometallic complexes involving bis(h-cyclopentadienyl)titanium(IV) and group 10 or 11 metal chlorides.; Polyhedron; Apr. 2000; pp. 757-764; Article: 3383.

Strohfeldt, Katja et al.; Bioorganometallic fulvene-derived titanocene anti-cancer drugs; Chemical Society Reviews; Apr. 2, 2008; pp. 1174-1187; vol. 37; The Royal Society of Chemistry; US.

Lease, Nicholas et al.; Potential Anticancer Heterometallic Fe—Au and Fe—Pd Agents: Initial Mechanistic Insights; Journal of Medical Chemistry; Jun. 20, 2013; pp. 5806-5818; vol. 56; American Chemical Society.

Pelletier, Frédéric et al.; Development of Bimetallic Titanocene-Ruthenium-Arene Complexes as Anticancer Agents:Relationships between Structural and Biological Properties; Journal of Medical Chemistry; Sep. 7, 2010; pp. 6923-6933; vol. 53; American Chemical Society.

Wenzel, Margot et al.; Multinuclear Cytotoxic Metallodrugs: Physicochemical Characterization and Biological Properties of Novel Heteronuclear Gold-Titanium Complexes; Inorganic Chemistry; Aug. 29, 2011; pp. 9472-9480; vol. 50; American Chemical Society; US.

*Primary Examiner* — Jennifer M Kim
(74) *Attorney, Agent, or Firm* — Peter J. Mikesell; Schmeiser, Olsen & Watts, LLP

(57) ABSTRACT

Titanocene-gold compounds are provided that are useful for treating cancers. The disclose compounds generally have a formula given by:

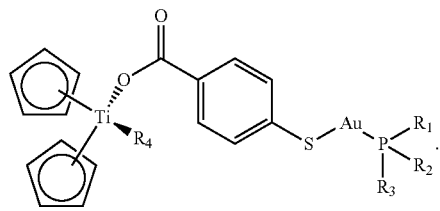

19 Claims, 12 Drawing Sheets

| IC$_{50}$ (μM) of compounds in cell lines at 24 hours (and 72 hours) incubation at 1% in DMSO and diluted with water | | | | | | |
|---|---|---|---|---|---|---|
| | Renal cancer cell lines | | | Non-tumorigenic kidney | Prostate | Prostate |
| Compound | A498 | UO31 | Caki-1 | HEK-293T | PC3 | DU145 |
| 2 | 2.94±0.46 (0.703±0.039) | 4.40±0.37 (0.067±0.04) | 3.37±0.25 (0.1162±0.003) | 64.42±7.91 (3.27±0.13) | 2.93±0.78 (1.296±0.4122) | 9.07±1.78 (0.76±0.24) |
| 6 | 25.08±6.3 (6.92±2.21) | 6.85±0.25 (0.41±0.21) | 10.36±4.1 (1.01±0.29) | 39.43±4.12 (27.66±5.30) | 48.18±6.22 (37.70±7.10) | 33.42±1.82 (6.63±1.84) |
| 7 | 8.72±1.77 (3.26±0.38) | 6.3±1.13 (1.41±0.09) | 6.07±1.77 (2.22±0.99) | 23.89±0.73 (6.94±2.42) | 48.21±12.0 (27.13±3.98) | 38.62±5.54 (35.48±1.45) |
| cisplatin | 74.73±6.05 (37.20±4.57) | >100 (8.91±2.76) | 68.79±0.145 (29±4.11) | 64.42±7.91 (3.27±0.13) | 91.69±17.97 (14.06±2.35) | 44.57±0.33 (12.12±3.91) |
| Titanocene dichloride | >200 (>200) | >200 (>200) | >200 (>200) | >200 (>200) | >200 (>200) | >200 (>200) |
| Titanocene Y | >200 (29.63±2.79) | >200 (>200) | >200 (29.42±4.18) | >200 (>200) | >200 (58.12±11.2) | >200 (55.18±7.87) |

FIG. 5

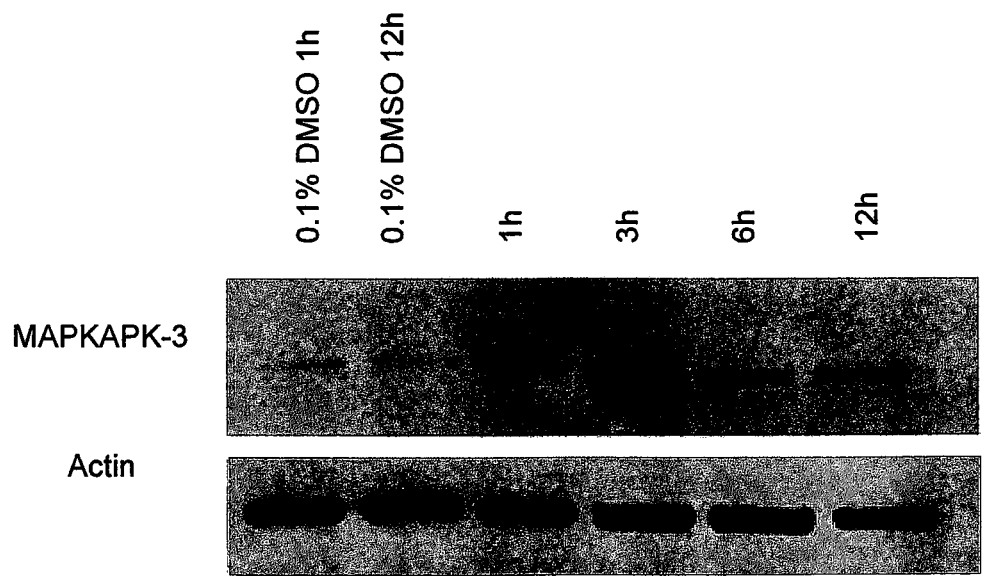
FIG. 14A  Compound 6
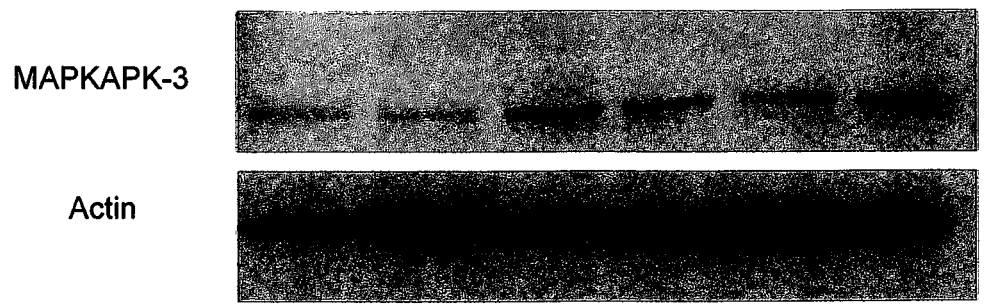
FIG. 14B  Compound 2
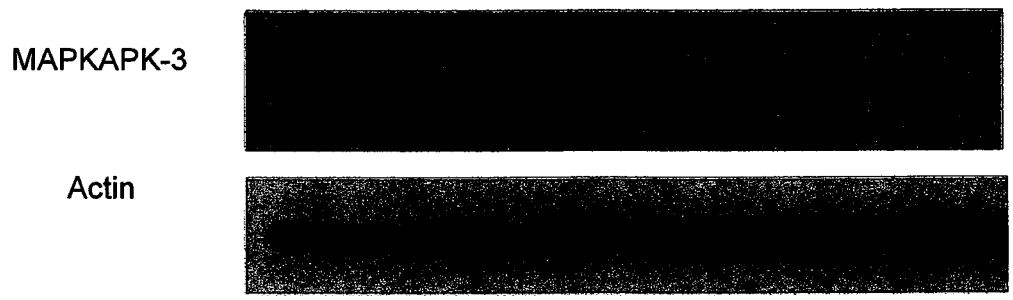
FIG. 14C  Auranofin

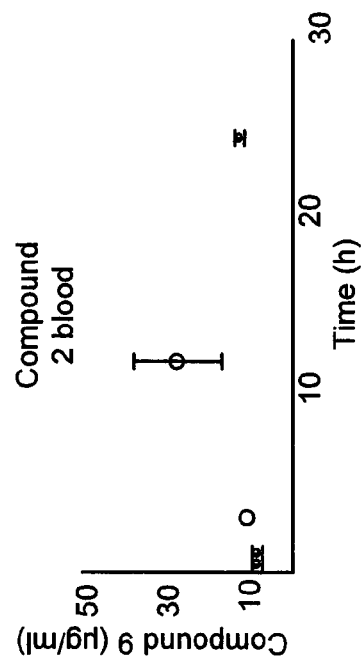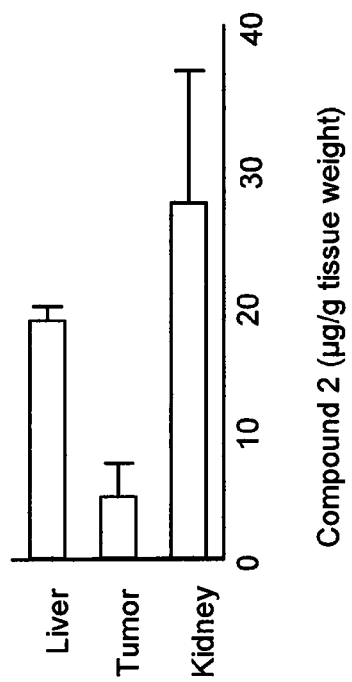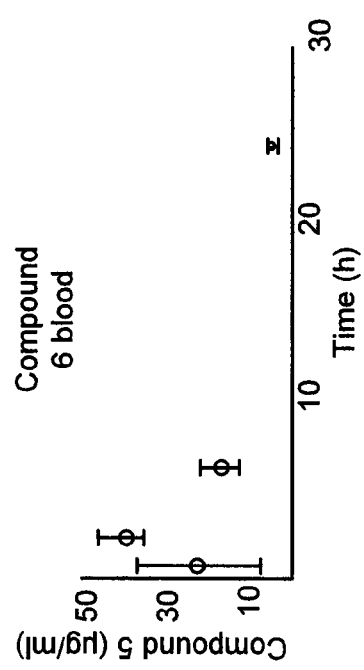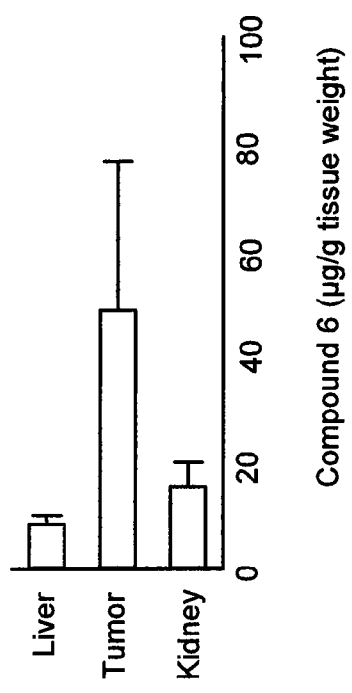
FIG. 15A
FIG. 15B
FIG. 15C
FIG. 15D

TITANOCENE-GOLD DERIVATIVES COMPRISING THIOLATO LIGANDS

CROSS-REFERENCE TO RELATED APPLICATIONS

This application claims priority to and is a non-provisional of U.S. provisional patent application No. 62/008,272 (filed Jun. 5, 2014) the entirety of which is incorporated herein by reference.

STATEMENT OF FEDERALLY SPONSORED RESEARCH OR DEVELOPMENT

This invention was made with Government support under Contract number 41849 awarded by the National Institute of Health-National Cancer Institute and Contract number R01GM088266-A1 awarded by the National Institute of Health-National Institute of General Medical Sciences. The government has certain rights in the invention.

BACKGROUND OF THE INVENTION

The subject matter disclosed herein relates to heterometallic compounds for treating cancers and to titanium-gold complexes in particular.

Cisplatin and its follow-on drugs (carboplatin and oxaliplatin) are used to treat 40%-80% of cancer patients, alone or in combination chemotherapy. However, the effectiveness of these drugs is still hundred by clinical problems, including acquired or intrinsic resistance, a limited spectrum of activity and high toxicity leading to side effects. Promising anticancer activities of a variety of other metal complexes have been reported in the past two decades. Metallocene dihalides ($Cp_2MCl_2$, where Cp=cyclopentadienyl, M=Ti, V, Nb, Mo or Re) were the first organometallic compounds with antitumor properties to be identified. Titanocene dichloride was the first non-platinum metal complex to enter clinical trials in 1993. Titanocene dichloride exhibited considerable antitumor activity in vitro and in vivo, even against cisplatin-resistant cells and tumor that were generally difficult to treat. Unfortunately, the efficacy of titanocene dichloride in Phase II clinical trials in patients with metastatic renal cell carcinoma or metastatic breast cancer was too low to be pursued. Alternatives to titanocene dichloride include titanocene Y and titanocene T.

Gold complexes are also a promising family of metallodrugs. In particular, a number of gold compounds have overcome cisplatin resistance to specific cancer cells. In addition, DNA is not the primary target for most gold compounds which reinforces the idea that their mode of action is different with respect to cisplatin.

Although titanium compounds and gold compounds have each received widespread attention, neither is entirely satisfactory in all situations. Improved alternatives are therefore desired. The discussion above is merely provided for general background information and is not intended to be used as an aid in determining the scope of the claimed subject matter.

BRIEF DESCRIPTION OF THE INVENTION

Titanocene-gold compounds are provided that are useful for treating cancers.

In a first embodiment, a method for providing a therapeutic benefit for a subject having a cancer is provided. The method comprises administering to the subject a compound of Formula (A), a stereoisomer, geometric isomer or pharmaceutically acceptable salt or pro-drug therefor, the compound comprising Formula (A)

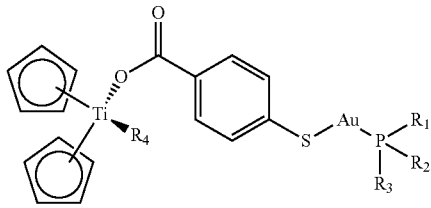

wherein $R_1$, $R_2$ and $R_3$ are each independently selected arenes; and $R_4$ is an alkane with between one and four carbons.

In a second embodiment, a compound for providing a therapeutic benefit for a subject having a cancer is provided. The compound comprises Formula (A)

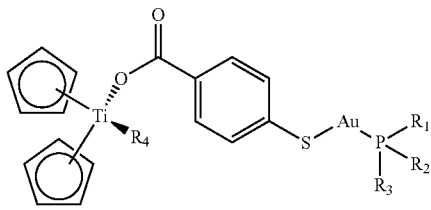

wherein $R_1$, $R_2$ and $R_3$ are each independently selected arenes; and $R_4$ is an alkane with between one and four carbons.

In a third embodiment, a compound for providing a therapeutic benefit for a subject having a cancer is provided. The compound comprises Formula (A)

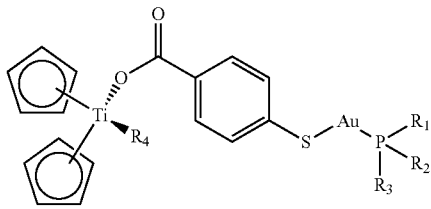

wherein $R_1$, $R_2$ and $R_3$ are each phenyl; and $R_4$ is ethyl or methyl.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 5 is table showing $IC_{50}$ (μM) values for select compounds against various cell lines;

FIGS. 14A, 14B and 14C are Western blots of Caki-1 cells exposed to compound 6, compound 2 and Auranofin, respectively;

FIGS. 15A and 15B depict plasma concentration of compounds 6 and 2, respectively, in blood; and FIGS. 15C and 15D depict accumulation of compound 6 and 2, respectively, in various tissues.

DETAILED DESCRIPTION OF THE INVENTION

Figure 1:
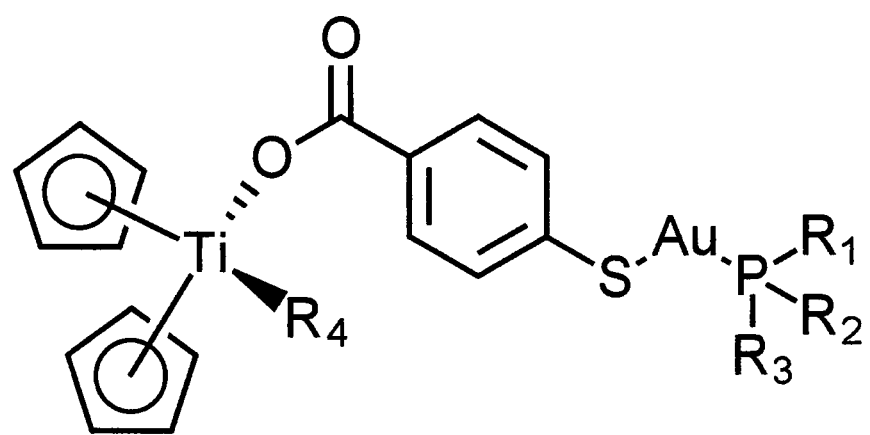
FIG. 1 is generic depiction of structural features for some exemplary titanocene-gold compounds useful in treating cancers.

As shown in FIG. 1, the subject matter disclosed in this specification pertains to heterometallic complexes comprising titanium and gold having the general formula:

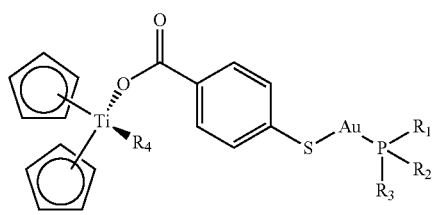

The disclosed heterometallic complexes display high activity against cancers and display particularly high activity against renal caners. Such compounds are more stable in physiological media than similar prior art compounds and are highly cytotoxic against human cancer renal cell lines. Several exemplary embodiments are depicted below.

Figure 2:
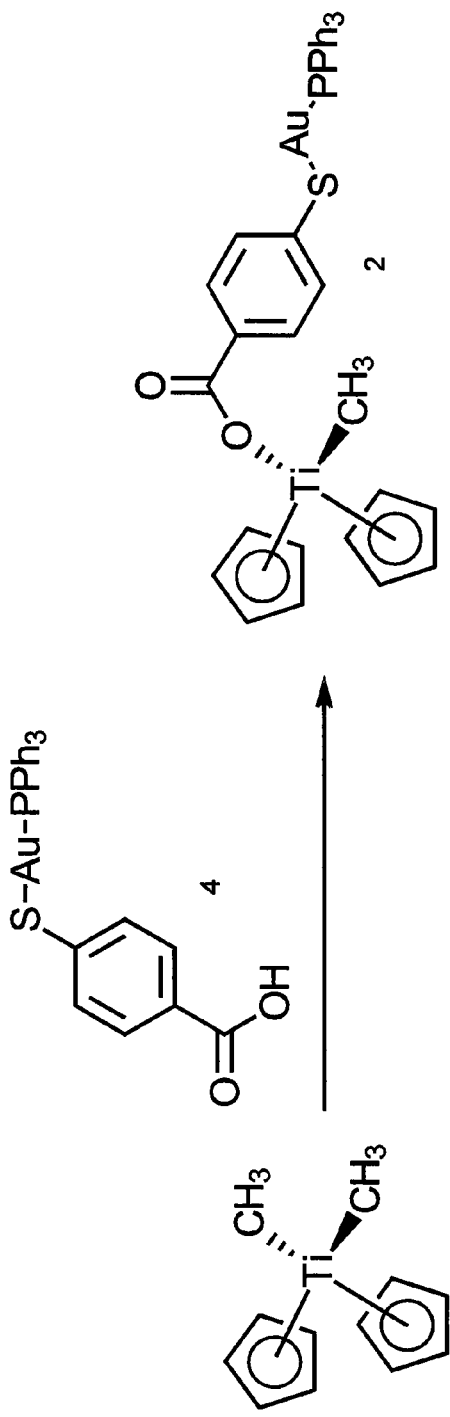
FIG. 2 is a synthetic scheme for select titanocene-gold compounds that are useful for treating cancers.
Figure 3:
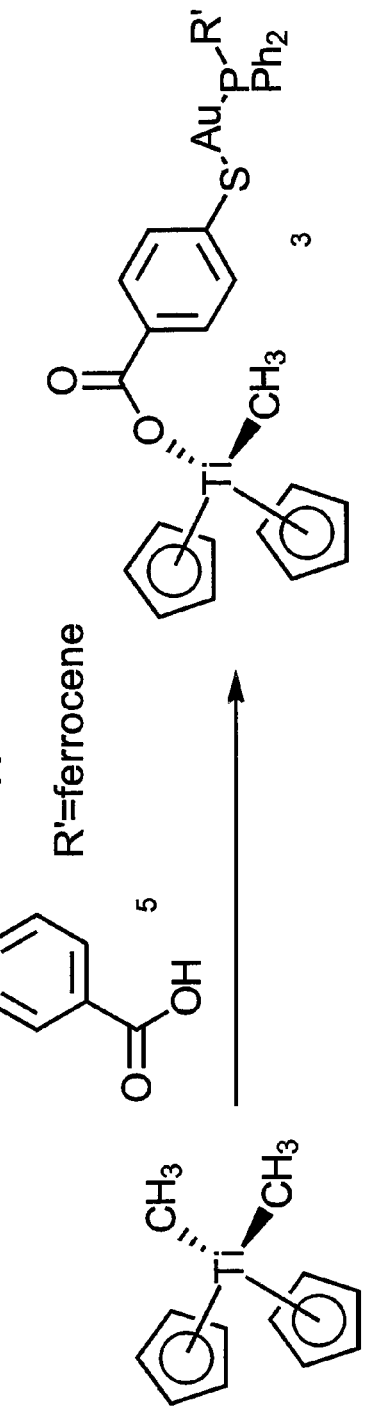
FIG. 3 is another synthetic scheme for select compounds that are useful for treating cancers.

By way of example, compounds 2 and 3 (shown below) are considerably more toxic to renal cancer cell lines (Caki-1 cells) than cisplatin, titanocene dichloride and Titanoscene Y. The synthesis of compound 2 and compound 3 is shown in FIG. 2 and FIG. 3. Surprisingly, the synthesis of compound 2 and compound 3 did not yield the expected binuclear $TiAu_2$ species and instead left one alkane bound to titanium. The small size of titanium may be the reason the di-substitution reaction did not proceed and bimetallic compounds (TiAu) were obtained instead of trimetallic compounds ($TiAu_2$).

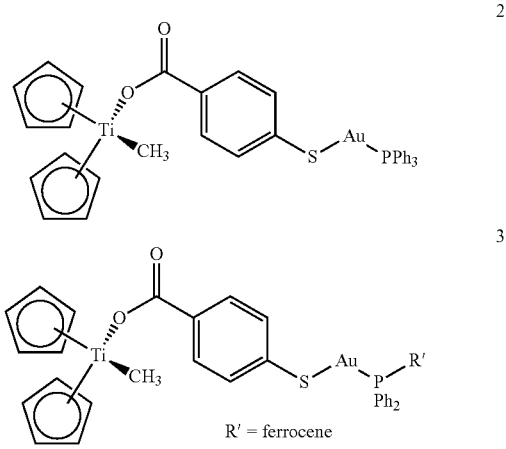

The effects of compound 2 and its non-sulfide analog compound 6 in Caki-1 mouse xenografts were examined using eighteen female NOD.CB17-Prkdc scid/J (non-obese diabetic—severe combined immunodeficiency) were selected for the in vivo trial.

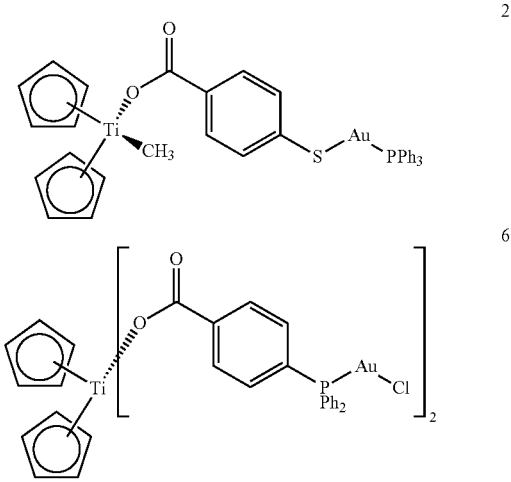

Figure 4:
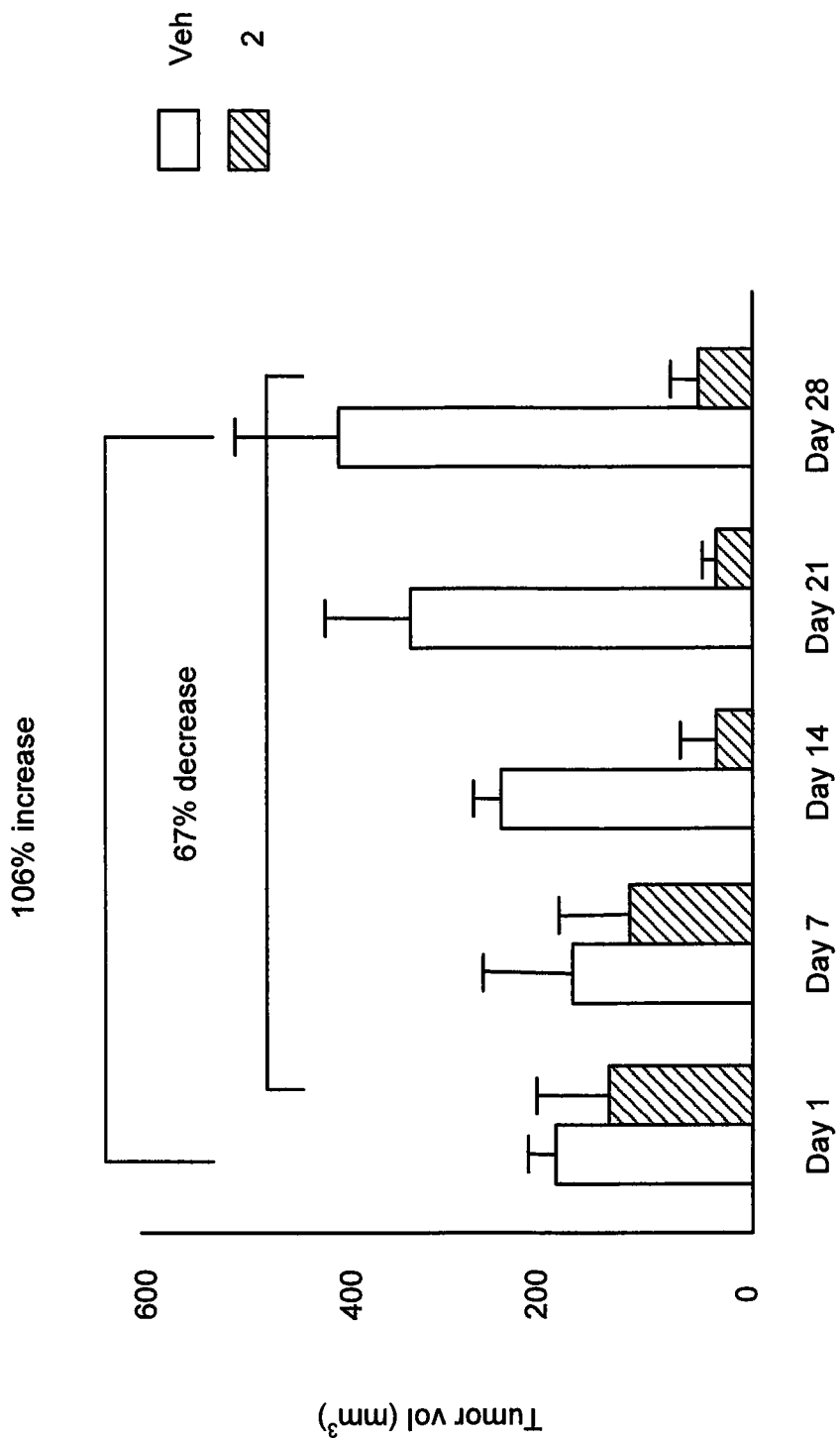
FIG. 4 is a graph depicting the change in tumor size after treatment with a control and with compound 2.

As shown in FIG. 4, the group treated with compound 2 showed an impressive decrease in tumor size (shrinkage) of 67% was observed from the starting volume between day 1 and day 28 of treatment (after a total of 14 doses). In contrast, in the control vehicle-treated group a 106% increase in tumor volume was observed between day 1 and day 28 of treatment (see Table 1). There was no weight loss in mice treated with treated with either compound 6 or compound 2 by this protocol. In the group treated with compound 6, no decrease in tumor size was observed nor was any hindrance in tumor growth from the starting volume observed between days 1 and day 28 of treatment (after a total of 14 doses). For compound 6 a 90% increase in tumor volume was observed.

TABLE 1

Effects of compound 2, compound 6 and the control vehicle on the tumour growth of Caki-1 renal carcinoma in NOD.CB17-Prkdc scid/J mice.

| Treatment group | | Primary Tumor (mm³) |
|---|---|---|
| Control | | 397.07 ± 14.96 |
| Compound 6 | 7.5 mg/kg/e.o.d$^a$ (×14) | 311.11 ± 9.45 |
| Compound 2 | 3 mg/kg/e.o.d$^a$ (×14) | 41.33 ± 13.00 | e.o.d = every other day.
Tumor measured on day 28, after 14$^{th}$ dose.

The results clearly indicate that compound 2 is extremely efficient in vivo since it not only inhibits tumor growth but it decreases the size of the tumors by 67%.

Table 2 provides IC$_{50}$ data for compound 2 and compound 3 against various cell lines. The heterometallic compound 2 is far more toxic in the nanomolar range than its monometallic gold precursor 4 (see FIG. 5) on these cells. Compound 2 is considerably less toxic to the non-tumorigenic human embryonic kidney cell line (HEK-293T) and human renal proximal tubular cells than is precursor 4. Compound 3 exhibits cytotoxicity with both Caki-1 and non-tumorigenic cell lines similar to that of its monometallic gold precursor 5 (see FIG. 3) but is less selective than compound 2 after 72 h incubation. The effect of combining monometallic gold precursor 4 and titanocene dichloride in renal cancer cell lines at 24 h showed IC$_{50}$ values greater than 100 µM. This demonstrates a synergistic effect for the heterometallic complexes in their in vitro activity on renal cancer cell lines.

TABLE 2

| | IC$_{50}$ values (µM) in human cells lines | | |
|---|---|---|---|
| | Caki-1 | HEK-293T | RPTC |
| Precursor 4 | 2.76 ± 0.35 | 1.11 ± 0.65 | 3.87 ± 0.15 |
| Compound 2 | 0.12 ± 0.003 | 0.49 ± 0.0008 | 2.67 ± 0.12 |
| Precursor 5 | 3.6 ± 0.342 | 3.0 ± 0.07 | 3.78 ± 0.13 |
| Compound 3 | 4.11 ± 0.64 | 3.09 ± 0.003 | 3.76 ± 0.21 |
| Cisplatin | 29 ± 4.11 | 3.27 ± 0.13 | — |
| [(π-C$_5$H$_5$)$_2$TiCl$_2$] | >200 | >200 | — |
| Titanocene Y | 29.42 ± 4.18 | >200 | — |

The samples used in Table 2 were prepared as 1% in DMSO and diluted with water before addition to medium for 72 h incubation period. Cisplatin and titanocene dichloride were dissolved in water. Compound 2 is toxic to all the cell lines studied. The IC$_{50}$ for some cell lines (e.g. UO31) is in the nanomolar range (72 h). However, the toxicity of compound 2 in the non-tumorigenic human embryonic kidney cell line (HEK-293T) is high as well. Compound 2 is selective to UO31 and CAKI-1 cell lines with respect to HEK-293T at 72 hours.

Both compound 2 and compound 3 were less acidic than titanocene dichloride and were soluble in DMSO/water, DMSO/PBS and DMSO/media (1:99) mixtures at micromolar concentrations. These compounds were unusually stable methyl-containing titanocene moieties that were stable as solids at room temperature, while exposed to air in CDCl$_3$ solution for at least five days. The half-lives of compound 2 and compound 3 in DMSO-d$_6$ are eight hours and thirty-two hours, respectively (sixteen-fold and sixty-four fold larger than for corresponding compound 6 and compound 7 (described elsewhere in this specification) in the same solvent). Surprisingly, the methyl groups of compounds 2 and 3 hydrolyzed at the same rate as the cyclopentadienyl groups. Therefore, the longer half-life found for compounds 2 and 3 in DMSO-d$_6$ could indicate the positive influence of the di-covalent linker between the titanium and the gold centers. The UV-vis spectra of compounds 2 and 3 (micromolar concentration in 1:99 DMSO/PBS solution did not change over time (23 h) indicating the hydrolysis is much slower in solutions at physiological pH.

Figure 6:
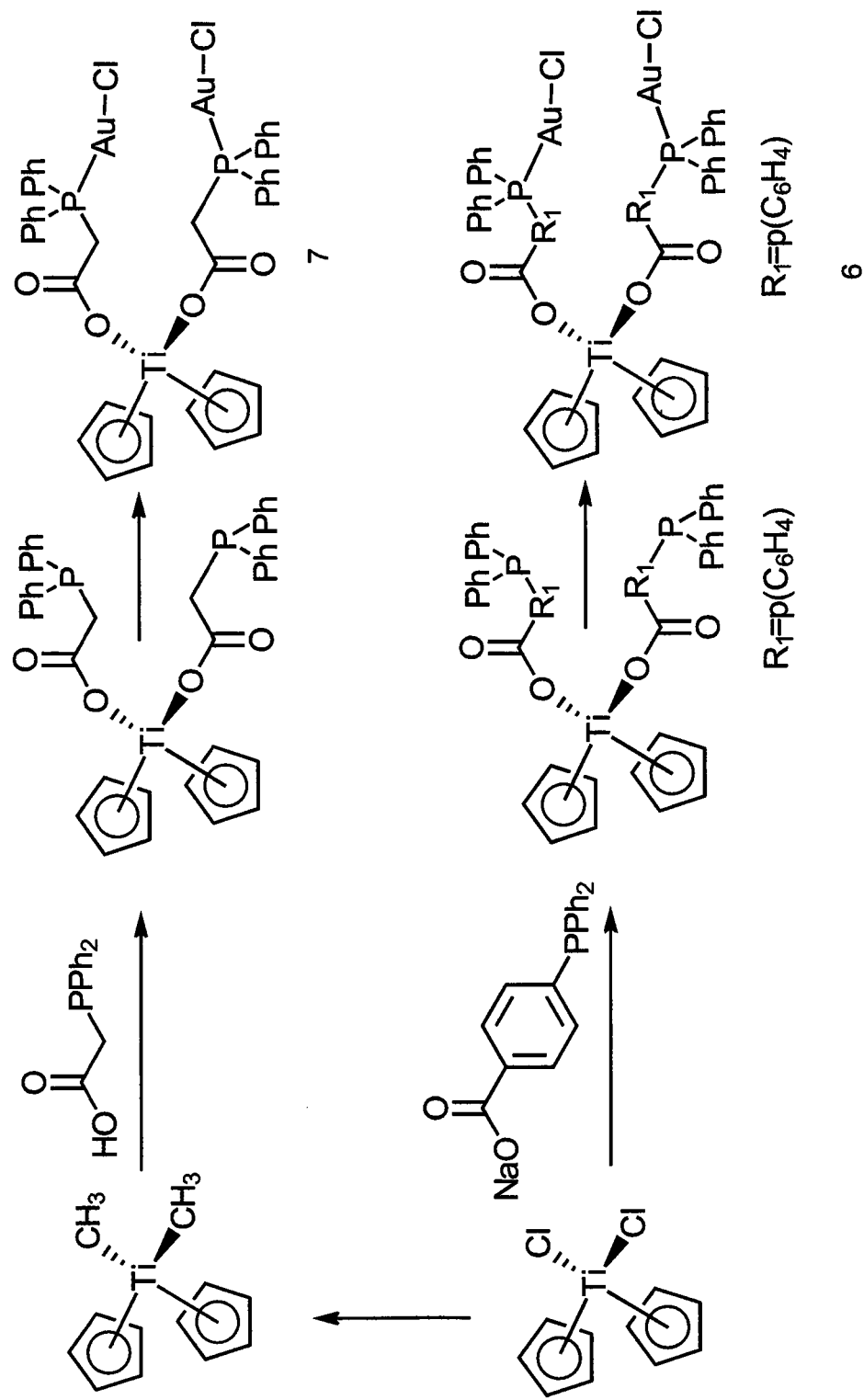
FIG. 6 is a synthetic scheme for two related titanocene-gold compounds that are useful for treating cancers.

As shown in FIG. 5, compound 6 and compound 7 are active against renal cancers in vitro, notwithstanding the in vivo results from the mouse xenograft experiments. An example of a synthetic scheme for forming compound 6 and compound 7 is shown in FIG. 6.

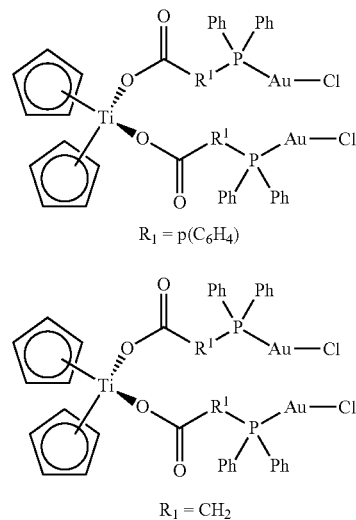

Figure 7:
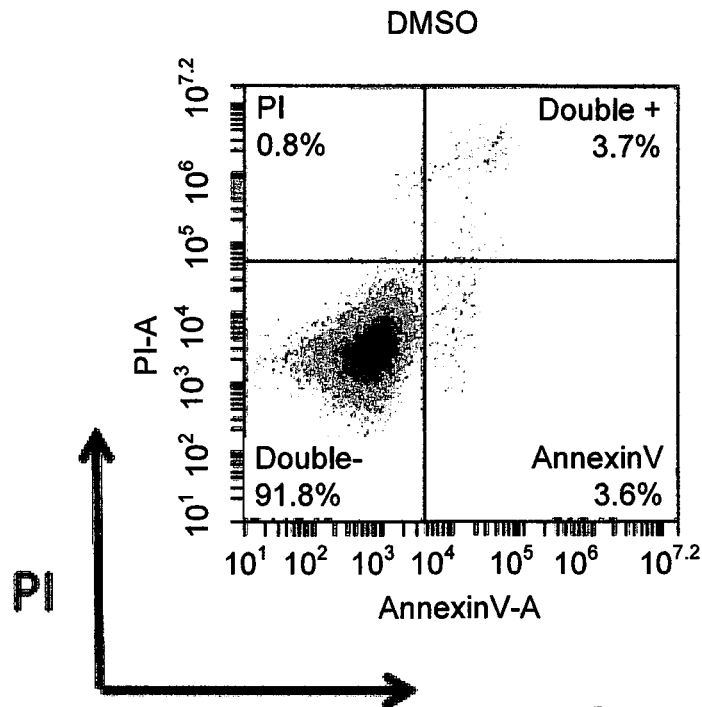
FIG. 7 shows the results of an apoptosis assay of a 1% solution in media that functions as a control.
Figure 8:
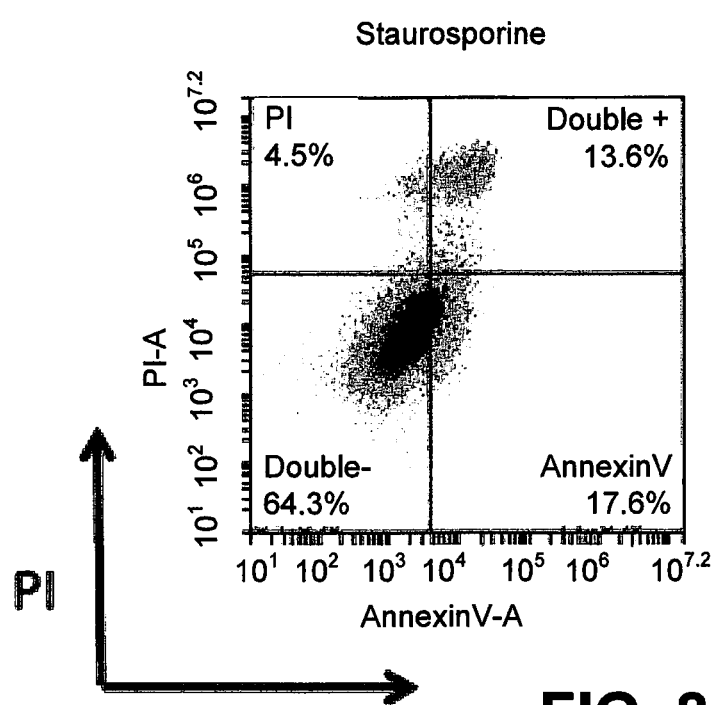
FIG. 8 shows the results of an apoptosis assay of a staurosporine media that functions as a control.
Figure 9:
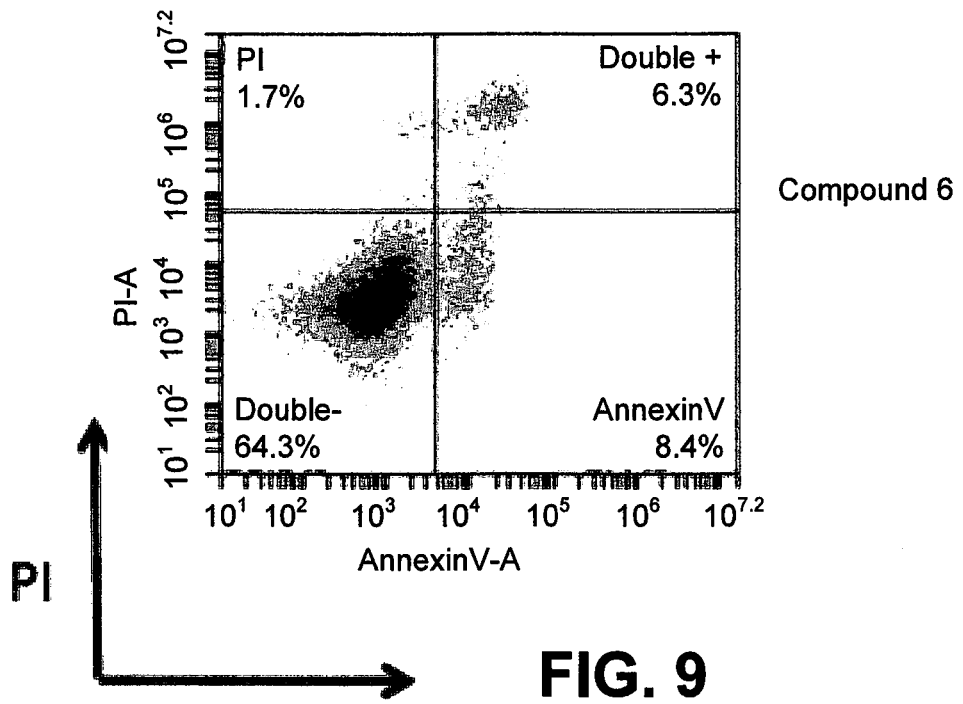
FIG. 9 shows the results of an apoptosis assay of compound 6.
Figure 10:
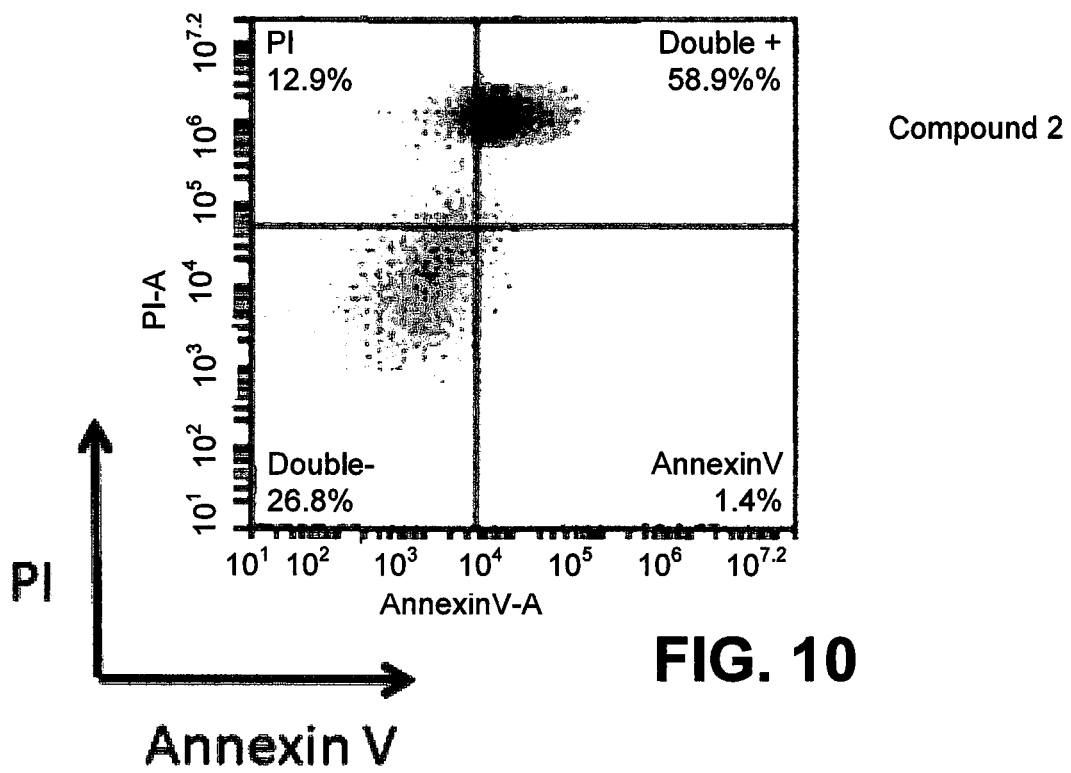
FIG. 10 shows the results of an apoptosis assay of compound 2.

To gain insight concerning the type of cell death that is induced in cancer cell lines, apoptosis assays were performed with Caki-1 cells with compound 2 dissolved in 1% DMSO solution in media. A 1% solution in media (FIG. 7) and staurosporine (FIG. 8) were used as controls. In early stages of apoptosis, one of the significant biochemical features is loss of plasma membrane phospholipid asymmetry due to translocation of phosphatidylserine (PS) from cytoplasmic to extracellular side. This characteristic allows detection of externalized PS by the specific binding of Annexin V (FITC-conjugated). Initiation of cell death will eventually result in the permeabilization of the cell membrane, allowing Pi to stain DNA within the nucleus. As shown in FIG. 7 (control), FIG. 8 (control), FIG. 9 (compound 6) and FIG. 10 (compound 2) each histogram is divided into four quadrants with the left top quadrant detecting necrotic cells without Annexin-V FITC signal. The right top quadrant shows cells with compromised membranes that are permeable to PI and stained with Annexin V-FITC which is indicative of late apoptosis. The left bottom quadrant shows live cells that have intact membranes (not stained) which the right bottom quadrant represents cells that were stained (bound) with Annexin V-FITC which is indicative of early apoptosis. After incubation during 6 hours with 10 μM of compound 2 necrosis can be clearly proposed. Compound 6 (with slower action on cancer cells as deduced previously from the in vitro $IC_{50}$ values at 24 h and 72 h) shows a pattern more in accordance with apoptosis (similar to staurosporine, an apoptotic agent).

Figure 11:
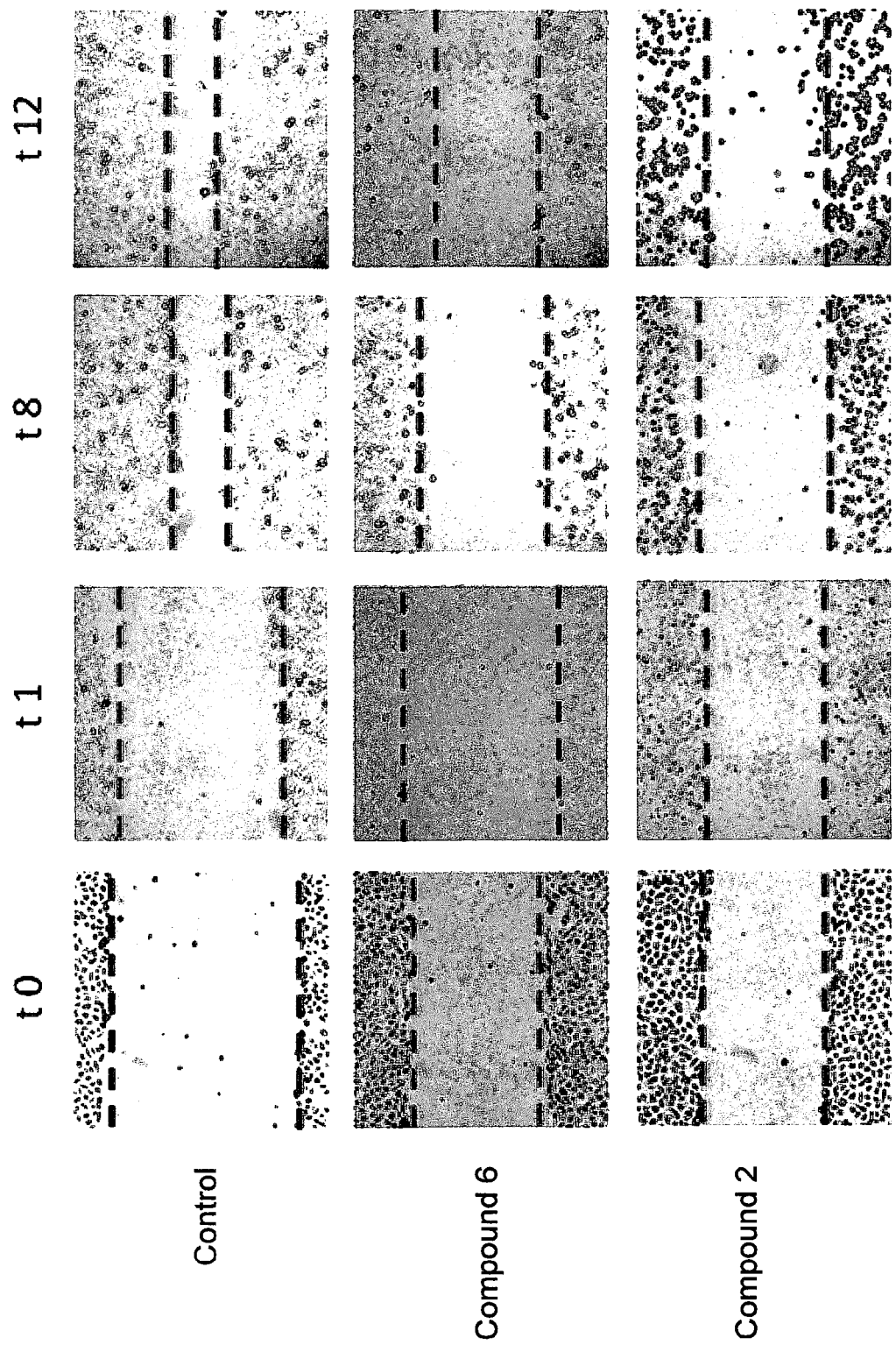
FIG. 11 is a wound-healing assay for compound 2, compound 6 and a control.

In advanced tumors, increased cell migration is a hallmark of cancer cell invasion and metastasis. Anti-invasive properties of the most active heterometallic titanocene-gold compound 2 and compound 6. Anti-invasive properties were evaluated by using a wound-healing scratch assay. Upon treatment with compound 6, cell migration was slowed with 81% of the scratch left uninvaded (see FIG. 11). However, in high metastatic CAKi-1 cells treated with 0.1% DMSO control, only 19% of the scratch remained uninvaded. As shown in FIG. 11, treatment of Caki-1 cells with compound 2 lead to complete inhibition of migration. Striking morphological changes occurred in cells treated with compound 2. Specifically, compound 2 caused distinct rounding of the cells and, after 12 hours of incubation, there was a complete loss of cell-cell contacts. These results clearly indicate anti-migratory properties for compound 2 and compound 6.

Figure 12:
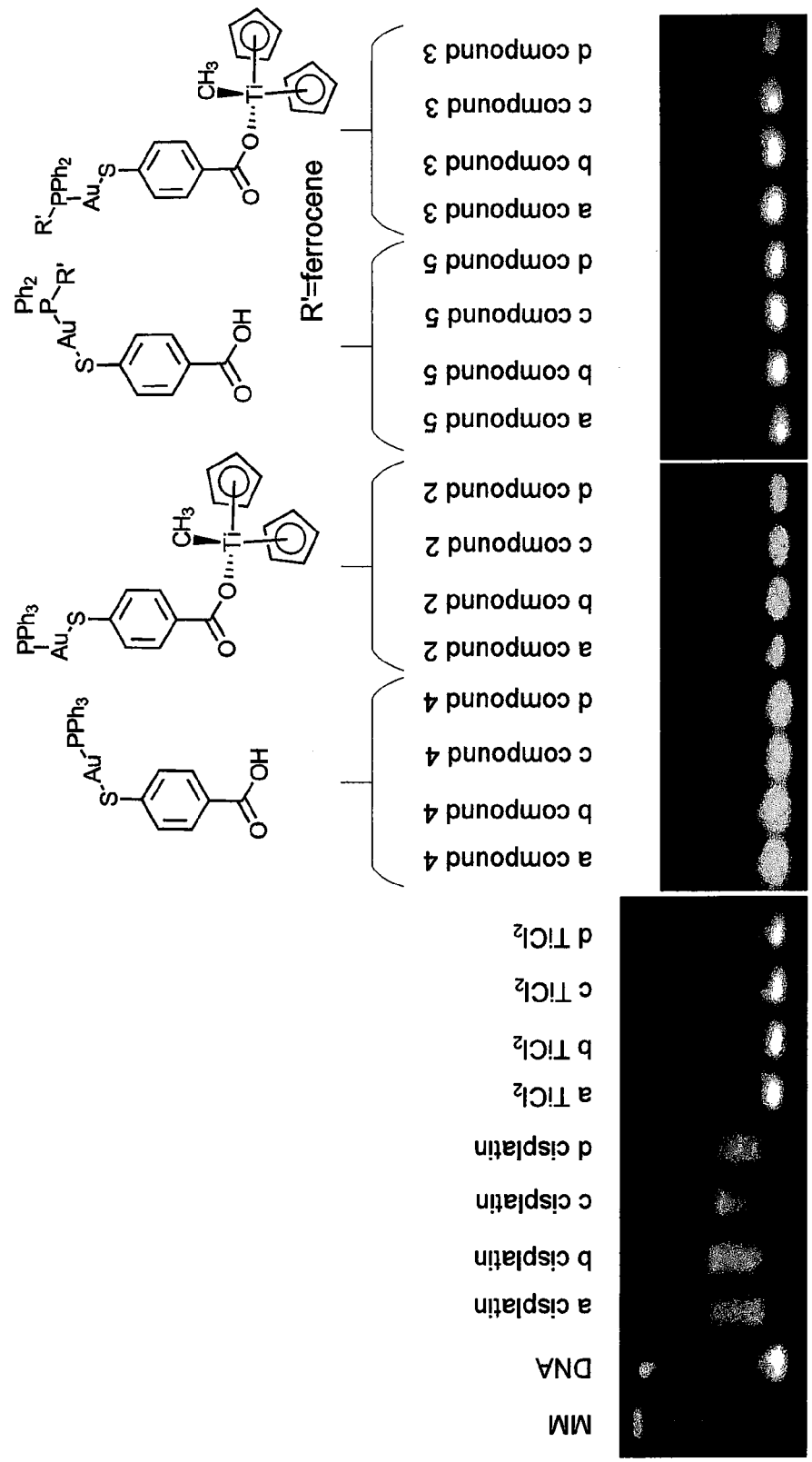
FIG. 12 depicts electrophoresis mobility shift assays for cisplatin, titanocene dichloride, compounds 4, 2, 5 and 3 run against untreated plasmid pBR322 DNA.

Because DNA replication is a key event for cell division, molecules that target DNA replication are important targets in cancer chemotherapy. DNA-interactions were tested with heterometallic compound 2 and compound 3, monometallic gold(I) derivatives 4 and 5, titanocene dichloride, or cisplatin by using plasmid (pBR322) DNA. This plasmid has two main forms: OC (open circular or relaxed form, Form II) and CCC (covalently closed or supercoiled form, Form I). Agarose gel electrophoresis assays were performed whereby decreased electrophoretic mobility of both forms were taken as evidence of metal-DNA binding. See FIG. 12 that depicts electrophoresis mobility shift assays for cisplatin, titanocene dichloride, compounds 4, 2, 5 and 3 run against untreated plasmid pBR322 DNA. Columns 1, b, c and 1 corresponding to metal/DNAbp ratios of 0.25, 0.5, 1.0 and 2.0 respectively. Generally, the slower the mobility of supercoiled DNA (CCC, Form I), the greater the DNA unwinding produced by the drug. For example, binding of cisplatin to plasmid DNA results in decreased mobility of the CCC form and increased mobility of the OC form. Treatment of plasmid DNA with increasing amounts of monometallic Au(I) compounds 4 and 5 or heterometallic TiAu compound 2 and compound 3 did not affect the mobility of the faster-running supercoiled form (Form I) even at the highest molar ratios (1:2 ratio).

Figure 13:
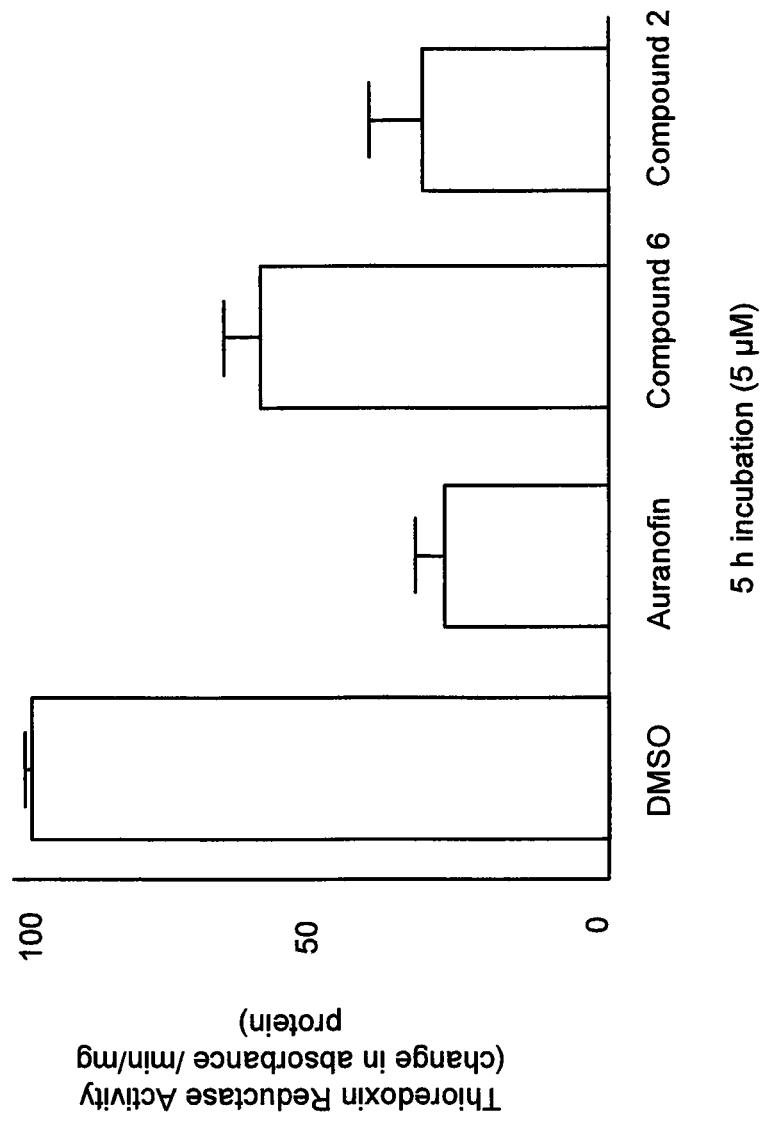
FIG. 13 is a graph depicting TrxR activity after treatment with select compounds.

Changes in cell anti-oxidant capacity are a characteristic of many chemo-resistant cancers, and overexpression of thioredoxin reductase (TrRx)) in drug-resistant cells is part of a defense and survival mechanism of cisplatin-resistant cells, thus making this enzyme an important anti-cancer target. A number of gold (I) compounds with anticancer properties are known to inhibit thioredoxin reductase isolated from human placenta, rat liver or isolated from treated cancer cells. One such example is a gold-thiolato-phosphane compound (Auranofin AF) which inhibits 50% of the enzymatic activity of isolated TrRx at concentrations as low as 20 nM. Auranofin also inhibits TrRx in human breast MCF-7 cancer cells (4 μM inhibits 18% total TrRx activity) and human ovarian A2780 cancer cells (10 μM inhibits 30% total activity). The activity of thioredoxin reductase in Caki-1 cells was measured, following incubation with compounds 2, 6 and Auranofin was used as a positive control. Thioredoxin reductase activity was found to be significantly lower in cells treated with 5 μM of compound 2, compound 6 or Auranofin with an observed inhibition of 31.6%, 68.2%, and 74.1% respectively after a five hour incubation (FIG. 13). The half maximal inhibitory concentration ($IC_{50}$) values were: 0.61 (±0.002) μM for Auranofin, 4.75 (±0.048) μM for compound 6, and 0.88 (±0.008) μM for compound 2 after twelve hours. The similar values for AF and compound 2 imply that the two compounds have similar potencies in Caki-1 cells. However compound 2 is markedly more toxic to Caki-1 cells than Auranofin ($IC_{50}$=3.08±0.13 μM for AF vs 0.12±0.003 μM for compound 2) indicating that inhibition of TrRx is not the only factor involved in the cytotoxic mechanisms of these heterometallic compounds. The observed inhibitory effect of compound 6 and especially compound 2 on thioredoxin reductase activity in whole cell lysates indicates that this enzyme is a suitable selective target for cancer therapy with this type of compounds.

Whole cell lysates of Caki-1 cells treated with compounds 2 or 6 were also evaluated for their effects on the expression levels of selected protein kinases, namely p90-RSK, AKT and MAPKAPK3. Compound 2 produced dramatic decreases in expression of all three protein kinases by 12 hours post-treatment. In contrast, no loss of expression was noted following a similar treatment with compound 6. These findings indicated that compound 2 acts through a transcriptional or translational mechanism after the first hour of treatment, thereby displacing direct drug-kinase interactions that were observed in vitro. Because all three enzymes have been implicated in promoting cell migration and therefore are strong targets for anti-metastasis drugs, these findings predict that compound 2 would be effective in controlling metastatic potential of renal tumors.

In summary, compound 2 inhibits thioredoxin reductase and causes decreased expression of pro-motility enzymes such as p90-RSK, AKT, and MAPKAPK3 in Caki-1 cells. In contrast, compound 6 has a more modest inhibitory effect on TrRx in Caki-1 cells but does not affect expression of the pro-motility enzymes. Nevertheless, compound 6 was found to reduce the secretion of IL-6 in Caki-1 cells thereby supporting the hypothesis that some MAPKAPK2/3 inhibition does occur. When Auranofin was tested as a negative control compound for TrRx inhibition studies, it was found to inhibit TrRx in the same range as compound 2 but failed to down-regulate MAKPAPK-3 in Caki-1 cells. See FIG. 14A to 14C. Caki-1 cells were incubated with compound 6 (FIG. 14A), compound 2 (FIG. 14B) against corresponding 0.1% DMSO controls for the indicated times. The Caki-1 cells were then lysed and a Western blot analysis was performed with anti-MAPKAPK-3 antibody. Blots were probed with anti-β-Actin antibody as a control for protein loading. A corresponding Western blot analysis for Auranofin is shown in FIG. 14C.

The lethal dose (LD) and maximum tolerated doses (MTD) of compound 2 were evaluated in C57/BL6 mice (see experimental for details). The LD was determined to be 15 mg/kg/day for compound 6 and 6 mg/kg/day for compound 2. The MTD was determined to be 10 mg/kg/day for compound 6 and 5 mg/kg/day for compound 2, the dose at which the mice showed no visible signs of distress over the seven days course of treatment. The mice did not lose weight during the trial. Twenty-four hours after the last dose all mice used in the MTD study were euthanized and blood plasma, liver, spleen and kidneys were collected and used for histological analysis. Necropsies indicate that mice treated at 10 mg/kg/day with compound 6 and 5 mg/kg/day with compound 2 showed normal liver and slightly enlarged spleens.

In view of this data, the dose of 7.5 mg/kg/day for compound 6 and 3 mg/kg/day for compound 2 every other day to conduct the subsequent in vivo trials. The choice of compound 6 and compound 2 for a subsequent in vivo trial was based on their selectivity in vitro against renal cancer cell lines when compared to non-tumorigenic human kidney cell lines (HEK-293T and RPTC) and their favorable preliminary toxicity profile on C57BL/6 mice.

Bimetallic compounds can be detected and quantified by the estimate of both titanium and gold ions by Inductively Coupled Plasma Mass Spectrometry (ICP-MS). Content of compound 2 and compound 6 in blood and tissues was calculated from their gold content and normalized to the extraction efficiency of gold in the respective tissues and blood. The pharmacokinetic profile of compound 6 is summarized in Table 3.

TABLE 3

| Pharmacokinetic parameters | Values |
| --- | --- |
| $K_{abs}$ | 1.3 hr$^{-1}$ |
| $K_e$ | 0.1 hr$^{-1}$ |
| $t_{1/2e}$ | 7.4 hr |
| $t_{1/2abs}$ | 0.6 hr |
| $t_{max}$ | 2.2 hr |
| $C_{max}$ | 37.7 µg/mL |

Compound 6 was absorbed quickly into plasma ($t_{1/2abs}$=0.55 hr) and the peak plasma concentration was reached after two hours of dosing. The drug was eliminated slowly from the blood compartment with an elimination half-life ($t_{1/2e}$) of about 7.5 hours. The blood concentration of gold at 6 hours after the last dose of compound 6 was 24.1±2.6 µg/mL, which is lower (P less than 0.01) than the $C_{max}$ after the first dose and not significantly different (P greater than 0.1) from the blood concentration at six hours after the first dose. This suggests compound 6 does not accumulate in the blood. Conversely, compound 2 had slow absorption with a constant increase in blood levels of the drug up to twenty-four hours. At the time of the second dose (48 hours after the first dose), the blood concentration of compound 2 was 40.4±6.0 µg/mL.

At the end of the study, gold content in liver, kidney and tumor was determined for compound 6 and compound 2 treatments. The level of gold in liver and kidney was less than 15 µg/g tissue weight which the tumor concentration was about 50 µg/g. The high level in tumor suggests enhanced tumor accumulation of compound 6. Compound 2 accumulated in the liver and kidney to a more significant degree. See FIG. 15A to FIG. 15D.

EXPERIMENTAL

All compounds involving titanium centers were prepared and handled with rigorous exclusion of air and moisture under a nitrogen atmosphere by using standard nitrogen/vacuum manifold and Schlenk techniques. Solvents were purified by use of a PureSolv purification unit from Innovative Technology, Inc. Titanocene dichloride was purchased from Aldrich and 4-mercaptobenzoic acid from TCI America Inc. and used without further purification. Compound 4, [AuCl(tht)] and [AuCl(MPPF)] were prepared according to known literature methods.

[(η-C$_5$H$_5$)$_2$TiMe(µ-mba)Au(PPh$_3$)] (compound 2). Compound 4 (1.174 g, 1.91 mmol) was dissolved in tetrahydrofurane (15 mL) and added via cannula over a solution of Cp$_2$TiMe$_2$ (0.399 g, 1.91 mmol) in toluene (10 mL) to yield a bright orange solution that was stirred for 1 hour at room temperature. The solvents were then removed under reduced pressure and the crude washed with diethyl ether (3×10 mL). The heterometallic complex that was isolated as a pale orange solid in 85% yield (1.312 g).

[Au(Hmba)(MPPF)] (compound 5). 4-mercaptobenzoic acid (0.109 g, 0.70 mmol) and KOH (0.040 g, 0.70 mmol) were dissolved in 20 mL of a 4:1 EtOH/H$_2$O mixture giving rise to a pale yellow solution that was stirred at RT for 10 minutes becoming colorless. The addition of [AuCl(MPPF)] (0.426 g, 0.70 mmol) led to thick yellow suspension that was stirred for 1 hour at RT. After solvents removal, the crude was washed with water (3×5 mL) and a 9:1 n-Hexane/Et$_2$O mixture (3×10 mL). Compound 6 was then isolated as a fine yellow solid in 89% yield (0.455 g). Crystals of compound 6 were obtained from a solution of compound 6 in CH$_2$Cl$_2$ layered with n-hexane at RT as orange prisms.

[(η-C$_5$H$_5$)$_2$TiMe(µ-mba)Au(MPPF)] (Compound 3). Compound 5 (0.402 g, 0.56 mmol) was dissolved in acetonitrile (15 mL) and added via cannula over a solution of Cp$_2$TiMe$_2$ (0.117 g, 0.56 mmol) in toluene (5 mL) to yield an orange solution that was stirred for 1 hour at RT. The solvents were then removed under reduced pressure and the crude washed with diethyl ether (3×10 mL). The heterometallic complex that was isolated as an orange solid in 81% yield (0.415 g).

Cell Culture: Human renal cell carcinoma lines A498, Caki-1 and UO31, as well as the human prostate carcinoma cell lines DU145 and PC3 were newly obtained for these studies from the American Type Culture Collection (ATCC) (Manassas, Va., USA) and cultured in Roswell Park Memorial Institute (RPMI-1640) (Mediatech Inc., Manassas, Va.) media containing 10% fetal bovine serum (FBS, Life Technologies, Grand Island, N.Y.), 1% Minimum Essential Media (MEM) nonessential amino acids (NEAA, Mediatech) and 1% penicillin-streptomycin (PenStrep, Mediatech). HEK-293T cells were newly purchased from ATCC (Manassas, Va., USA) and maintained in Dulbecco's modified Eagle's medium (DMEM) (Mediatech) supplemented with 10% FBS, 1% NEAA and 1% PenStrep. Normal human renal epithelial cells (RPTC) were purchased from Lifeline Cell Technology (Lifeline Cell Technology, Frederick, Md., USA) and maintained in Lifeline's Renal Life Medium from Lifeline Cell Technology supplemented with 2.4 mM L-glutamine, 5 µg/mL rh insulin, 1.0 nM epinephrine, 10 nM triiodothyronine, 0.1 µg/mL hydrocortisone hemisuccinate, 10 ng/mL rhEGF, 0.50% FBS, 5 µg/mL transferrin PS. All cells were cultured at 37° C. and 5% CO$_2$ in a humidified incubator.

Cell Viability Assay: Cells were seeded at a concentration of 5000 cells/90 µl per well of either RPMI or DMEM without phenol red and without antibiotics, supplemented with 10% FBS and 2 mM L-glutamine into tissue culture grade 96-well flat bottom microplates (BioLite Microwell Plate, Fisher Scientific, Waltham, Mass., USA) and grown for 24 h at 37° C. in a humidified incubator. Afterwards, the intermediate dilutions of the compounds were added to the wells (10 µL) to obtain a final concentration ranging from 0.1 to 200 µM, and the cells were incubated for 24 h or 72 h. Following 24 h or 72 h drug exposure, 50 µL per well of 2,3-bis-(2-methoxy-4-nitro-5-sulfophenyl)-2H-tetrazolium-5-carboxanilide (XTT) (Roche Diagnostics, Indianapolis, Ind., USA) labelling mixture was added to the cells at a final concentration of 0.3 mg/ml and incubated for 4 h at 37° C. in a humidified incubator. The optical absorbance of each well in a 96-well plate was quantified using BioTek ELx808 absorbance microplate reader (BioTek Winooski, Vt.) set at 450 nm wavelength. The percentage of surviving cells was calculated from the ratio of absorbance of treated to untreated cells. The IC$_{50}$ value was calculated as the concentration reducing the proliferation of the cells by 50% and is presented as a mean (±S.E.) of at least two independent experiments each with triplicate measurements.

Annexin V/PI assay: Confluent Caki-1 cells were treated with either 10 of compound 2, 0.1% DMSO or 5 μM of staurosporine for 6 h. After incubation, cells were trypsinized with 0.25% trypsin without EDTA (Life Technologies, NY, USA) and stained for extracellular phosphatidylserine expression using FITC conjugated annexin V to label early apoptotic cells and co-stained with propidium iodide (PI) to identify necrotic cells according to the manufacturer instructions for the dyes (BD Biosciences, San Jose, Calif.). Stained cells were analyzed by flow cytometry using Accuri C6 software (BD Biosciences, San Jose, Calif., USA).

Cell migration: For wound healing assays, Caki-1 cells were seeded in 6 cm dishes at a density of $0.8 \times 10^6$ in complete media, then grown to confluence for twenty-four hours at 37° C. (5% $CO_2$), then cross-shape wounds/scratches were performed in the monolayer using a sterile 10 μl pipette tip. Following the treatment of confluent cells with 5 μM compound 6 or compound 2 or 0.1% DMSO as control, images of wounds were captured by light microscopy using the Labomed TCM 400 Inverted Research Microscope (Abo America Inc., Fremont, Calif.) and a digital Moticam 10 camera(Fisher Scientific Pittsburgh, Pa.) immediately after scratching (T0), after 1 hour (T1) and after 12 h (T12). To quantify cell migration, the area of the initial wound (T0) is compared with the area of the healing wound at three time points after the scratch is introduced. Percent Migration=[area of original wound−area of wound during healing]/Area of original wound]×100.

Mobility Shift Assay: 10 μL aliquots of pBR322 plasmid DNA (20 μg/mL) in buffer (5 mM Tris/HCl, 50 mM $NaClO_4$, pH=7.39) were incubated with different concentrations of the compounds (2, 3, 4, 5), and titanocene dichloride) (in the range 0.25 and 4.0 metal complex:DNA bp) at 37° C. for 20 h in the dark. Samples of free DNA and cisplatin-DNA were prepared as controls. After the incubation period, the samples were loaded onto the 1% agarose gel. The samples were separated by electrophoresis for 1.5 h at 80 V in Tris-acetate/EDTA buffer (TAE). Afterwards, the gel was stained for 30 min with a solution of GelRed nucleic acid stain.

Thioredoxin Reductase Inhibition Studies in Caki-1 cells: For thioredoxin reductase activity assays, whole cell lysates was obtained from Caki-1 cells treated in vitro with either 0.1 μM, 0.5 μM, 1 μM, or 5 μM of compound 2, compound 6 or Auranofin or 1% DMSO. After 5, 12 or 24 hours of treatment incubation cells were washed three times in PBS, and lysed by douncing using scrapers and sheer force though syringe with a 34 gauge needle in assay buffer (Abeam Thioredoxin Reductase Assay kit, ab83463) added to 1 mM protease inhibitor cocktail (Abeam, ab65621). The lysates were centrifuged at 10,000×g for 15 minutes at 4° C. to isolate insoluble material. The total protein concentrations of soluble lysates were measured using the BCA Protein Assay (Life Technologies). The soluble lysates were incubated for 20 minutes in assay buffer with a proprietary thioredoxin reductase specific inhibitor before adding a specific substrate, DTNB (5, 5'-dithiobis(2-nitrobenzoic) acid), and measuring activity at 1 minute intervals for 30 minutes using the BioTek fluorescence microplate reader (BioTek U.S., Winooski, Vt.) set at =412 nm. Lysates were tested in duplicate. TrxR activity was calculated based on the linear amount of TNB produced per minute per mg of total protein and corrected for background activity from enzymes other than TrxR in the lysates.

Kinase Inhibition Studies: In vitro profiling of a 35 selected member protein kinase panel was performed at Reaction Biology Corporation using the "HotSpot" assay platform. Briefly, specific kinase/substrate pairs along with required cofactors were prepared in reaction buffer; 20 mM Hepes pH 7.5, 10 mM $MgCl_2$, 1 mM EGTA, 0.02% Brij35, 0.02 mg/ml BSA, 0.1 mM $Na_3VO_4$, 2 mM DTT, 1% DMSO. Compounds were delivered into the reaction, followed about 20 min later by addition of a mixture of ATP (Sigma) and $^{33}$P-ATP (PerkinElmer) to a final concentration 10 μM. Reactions were carried out at 25° C. for 120 min, followed by spotting of the reactions onto P81 ion exchange filter paper (Whatman). Unbound phosphate was removed by extensive washing of filters in 0.75% phosphoric acid. After subtraction of background derived from control reactions containing inactive enzyme, kinase activity data were expressed as the percent remaining kinase activity in test samples compared to vehicle (dimethyl sulfoxide) reactions. $IC_{50}$ values and curve fits were obtained using Prism (GraphPad Software).

Cell lysis and immunoblotting: Caki-1 cells were seeded into 10-cm dishes at a density of $2.2 \times 10^6$ and incubated for 24 hours. Following the treatment of confluent cells with 5 μM of compound 6 and compound 2 and 0.1% DMSO as control for either 1 hour, 3 hours, 6 hours or 12 hours, the cultures were washed with cold PBS, and the cells were harvested by scraping with a rubber cell scraper. After microcentrifuging for 5 minutes at 4° C., pellets were treated with ice-cold lysis buffer with cell extraction buffer (BioSource, Camarillo, Calif.) containing 0.1% protease inhibitors and 1% phosphatase inhibitors cocktail (Fisher Scientific, Pittsburgh, Pa.) for 10 minutes, then sonicated for 10 seconds three times, and placed on ice. The lysed cells were centrifuged at 10,000×g at 4° C. for 10 minutes to remove the pellets representing the insoluble cell fraction.

The protein concentration was determined with BCA protein dye reagent (Pierce, Fisher Scientific Pittsburgh, Pa.). Samples were denatured with 5×SDS sample buffer (0.25% bromophenol blue, 0.5 M dithiothreitol (DTT), 50% glycerol 50% (v/v), 10% sodium dodecyl sulfate (SDS) followed by heating at 95° C. for 5 minutes. Proteins were separated by SDS-PAGE, transferred to a PVDF membrane (Millipore Corp.), and probed with MAPKAPK-3 antibody (Cell Signaling Technology, Danvers, Mass., USA), as well as β-actin antibody (Cell Signaling Technology, Danvers, Mass., USA). Immunoreactive bands of primary antibodies were detected using HRP goat anti-rabbit and secondary antibodies were detected with peroxidase-conjugated secondary antibody and detected by chemiluminescence (Pierce Biotechnology, Rockford, Ill.).

Lethal and maximum tolerated doses (LD and MTD): Determination of lethal and maximum tolerated doses (LD and MTD) in mice: The preliminary toxicity testing of compound 2 was performed in C57BL/6 female mice six to eight weeks of age, maintained in accordance with institutional guidelines at the University of Hawaii Cancer Center (UHCC) governing the care of laboratory animals (IACUC number: A3423-01). To determine the lethal dose, mice were treated for five consecutive days at dosages ranging from 1.5 mg/kg/day to 6 mg/kg/day. One mouse per dose was used. Mice were weighed every forty-eight hours, and sacrificed twenty-four hours after the last dose. The compounds were administered in a solution of 0.5% DMSO and 99.5% normal saline (0.9% NaCl) (G-Biosciences, St. Louis, Mo., U.S.A) once daily by subcutaneous injection. In order to determine the maximum tolerated dose (MTD) the animals were monitored by trained individuals for pain and distress as appropriate for the animal, under conditions and by procedures established by the UHCC vivarium veterinary staff and research personnel (BTE). The maximum tolerated dose (MTD) was determined by observing the progression of the mice treated at doses below the lethal dose. Body weights, changes in behavior and signs of distress were recorded. The dose at which neither debilitating effects nor sign of distress were observed was set as the MTD. More specifically the signs for distress monitored were: 1. Decreased food and water consumption; 2. Weight loss (more than 20% loss in body weight or dropping at or below 18 g) was consistent with significant distress and mice exhibiting such weight loss were euthanized; 3. Abnormal posture/positioning (e.g., head-pressing, hunched back); 4. Unkempt appearance (erected, matted, or dull haircoat); 5. Self-mutilation, gnawing at limbs; 6. Excessive self-imposed isolation/hiding. The MTD dose was confirmed by treating a cohort of three mice per compound and one control group, every other day for fourteen days with the MTD dose. One group of mice was treated with the solvent (negative control). During the trial the mice did not exhibit any signs of distress.

Study of the effects of 2 in Caki-1 xenografts in mice: twelve female NOD.CB17-Prkdc scid/J (non-obese diabetic—severe combined immunodeficiency) from Jackson Laboratory (Bar Harbor, Me. and Sacramento, Calif., USA) were used for the xenograft experiment (ages 8 to 12 weeks and weighing 19-22 g) were used. Each mouse received $8 \times 10^6$ tumor cells subcutaneously without anesthesia. Exponentially growing Caki-1 human kidney cancer cells were suspended in 1:1 ratio 50 µl phosphate-buffered saline (PBS; pH 7.4) plus 50 µl of matrigel (BD Biosciences, San Jose, Calif., USA) were injected subcutaneously on both left and right flank of each mice. The diameter of the tumors was measured once weekly using an electronic digital caliper and the tumor volume (TV) was calculated according to the empirical equation $TV=(a)(b^2) \times \pi/6$ where a=longest dimension; b=largest dimension orthogonal to a. The median volumes of each group were normalized to the initial tumor volume resulting in the relative tumor volume. Each group of six Caki-1-transplanted animals received compound 6 (7.5 mg/kg/every other day), compound 2 (3 mg/kg/every other day) or vehicle (0.1% DMSO in 0.9% NaCl) intraperitoneally (i.p.). Treatment started when tumors were palpable (about 6 mm diameter). Mice were randomized to treatment groups based on their starting tumor burden at twelve weeks of age to ensure equivalent distribution between the three groups. At trial end-point the mice were sacrificed and tumors measured again after excision and then processed for further analysis. Histological as well as biochemical evaluations of blood, liver, spleen, and kidney, were conducted. Tumor volumes were graphed for compound 6 and compound 2 treated mice compared to vehicle-treated mice, based on weekly external digital caliper measurements.

Bio-distribution: determination of gold and titanium content in the organs and plasma: Female NOD.CB17-Prkdc scid/J bearing subcutaneous Caki-1 tumors and treated with subcutaneous injection of either compound 6 (7.5 mg/kg/48 hours) or compound 2 (3 mg/kg/48 hours) were used for pharmacokinetic distribution of the drug in blood and other tissues. Blood was collected by retro-orbital bleeding into heparinized blood collection vials on ice at time intervals of 30 minutes, 2 hours, 6 hours, 24 hours, and 48 hours after the first dose. The blood samples were centrifuged at 2800 rpm at 4° C. for 15 min and the supernatant plasma was transferred into 1.5 ml micro-centrifuge tubes and stored at −80° C. until further analysis.

Gold and titanium content was determined using ICP-MS. In brief, fifty microliters of plasma was transferred into a glass vial and 1 ml of concentrated acid mix (comprising of 75% of 16 N nitric acid and 25% of 12 N hydrochloric acid) was added. The mixture was heated at 90° C. for 5 hours. After cooling, the samples were diluted with water, 40 ppb of Indium internal standard was added and analyzed in a Thermo Scientific XSERIES 2 ICP-MS with ESI PC3 Peltier cooled spray chamber with SC-FAST injection loop and SC-4 autosampler. All the elements were analyzed using $He/H_2$ collision-reaction mode. Plasma from control mice was spiked with the test compounds to determine the extraction efficiency of gold and titanium.

At the end of the study, liver, kidney and tumor of the animals were harvested, weighed and transferred into glass vials. One ml of water was added to each samples and subjected to ultrasonic tissue disruption at 15 W power for 1 minute. The tissue homogenates were frozen at −80° C. for two hours and lyophilized. The lyophilized product was heated at 90° C. with the concentrated acid mix (described above) for five hours, cooled, diluted with water and analyzed for titanium and gold by ICP-MS. Pharmacokinetic estimates were obtained from the plasma concentration-time profiles by non-compartmental analysis.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A compound for providing a therapeutic benefit for a subject having a cancer, the compound comprising:

Formula (A)

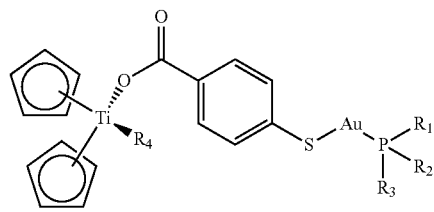

wherein:

$R_1$, $R_2$ and $R_3$ are each independently selected arenes; and $R_4$ is an alkane with between one and four carbons.

2. The compound as recited in claim 1, wherein $R_1$, $R_2$ and $R_3$ are the same.

3. The compound as recited in claim 1, wherein $R_1$ is a ferrocene.

4. The compound as recited in claim 1, wherein $R_1$ is a ferrocene, $R_2$ is phenyl and $R_3$ is phenyl.

5. The compound as recited in claim 1, wherein $R_4$ is methyl, ethyl, n-propyl or isopropyl.

6. The compound as recited in claim 1, where $R_4$ is ethyl or methyl.

7. The compound as recited in claim 1, where $R_4$ is methyl.

8. A compound for providing a therapeutic benefit for a subject having a cancer, the compound comprising:

Formula (A)

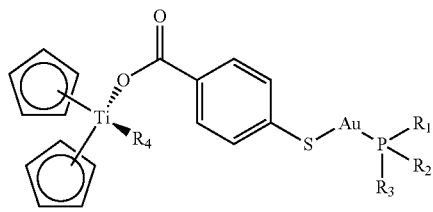

wherein:

$R_1$, $R_2$ and $R_3$ are each phenyl; and $R_4$ is ethyl or methyl.

9. The compound as recited in claim 8, wherein $R_4$ is methyl.

10. A method for providing a therapeutic benefit for a subject having a cancer, the method comprising administering to the subject a compound of Formula (A), a stereoisomer, geometric isomer or pharmaceutically acceptable salt thereof, the compound comprising:

Formula (A)

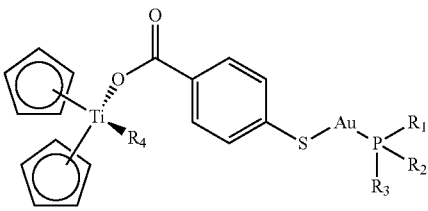

wherein:

$R_1$, $R_2$ and $R_3$ are each independently selected arenes; and $R_4$ is an alkane with between one and four carbons.

11. The method as recited in claim 10, wherein $R_1$, $R_2$ and $R_3$ are the same.

12. The method as recited in claim 10, wherein $R_1$ is phenyl.

13. The method as recited in claim 10, wherein $R_1$ is a ferrocene.

14. The method as recited in claim 10, wherein $R_1$ is a ferrocene, $R_2$ is phenyl and $R_3$ is phenyl.

15. The method as recited in claim 10, wherein $R_1$ is a ferrocene, $R_2$ is phenyl, $R_3$ is phenyl and $R_4$ is methyl.

16. The method as recited in claim 10, where $R_4$ is ethyl or methyl.

17. The method as recited in claim 10, where $R_4$ is methyl.

18. The method as recited in claim 10, wherein $R_1$, $R_2$ and $R_3$ are each phenyl, and $R_4$ is ethyl or methyl.

19. The method as recited in claim 10, wherein $R_1$, $R_2$ and $R_3$ are each phenyl, and $R_4$ is methyl.

* * * * *